US009726477B2

(12) United States Patent
Matsinos

(10) Patent No.: US 9,726,477 B2
(45) Date of Patent: Aug. 8, 2017

(54) METHOD AND APPARATUS TO PROVIDE CORRECTIONS FOR A RADIATION-THERAPY BEAM

(75) Inventor: Evangelos Matsinos, Schinznach-Dorf (CH)

(73) Assignee: Varian Medical Systems, Inc., Palo Alto, CA (US)

( * ) Notice: Subject to any disclaimer, the term of this patent is extended or adjusted under 35 U.S.C. 154(b) by 1814 days.

(21) Appl. No.: 12/652,248

(22) Filed: Jan. 5, 2010

(65) Prior Publication Data

US 2010/0171964 A1 Jul. 8, 2010

Related U.S. Application Data

(60) Provisional application No. 61/142,807, filed on Jan. 6, 2009.

(51) Int. Cl.
*G01B 11/24* (2006.01)
*A61N 5/10* (2006.01)
*G01B 21/20* (2006.01)

(52) U.S. Cl.
CPC ............ *G01B 11/24* (2013.01); *A61N 5/1031* (2013.01); *G01B 21/20* (2013.01)

(58) Field of Classification Search
USPC ................. 356/601–613; 250/492.1, 492.22; 378/64, 65, 68, 54, 70
See application file for complete search history.

(56) References Cited

U.S. PATENT DOCUMENTS

| 5,644,614 A * | 7/1997 | Toth ........................ A61B 6/032 378/145 |
| 7,872,760 B2 * | 1/2011 | Ertl ................................ 356/479 |
| 7,977,656 B2 * | 7/2011 | Fujimaki .................. H05H 7/10 250/492.3 |
| 2007/0165779 A1 * | 7/2007 | Chen et al. ..................... 378/65 |

* cited by examiner

*Primary Examiner* — Tri T Ton
(74) *Attorney, Agent, or Firm* — Fitch, Even, Tabin & Flannery LLP

(57) ABSTRACT

Information is provided regarding a block's sectional contour in a particular plane as corresponds to a radiation-therapy beam. For a point at which block effects are to be assessed, a point is projected onto a plane of the block and a plurality of straight lines is then formed. Each line has a particular relationship with respect to the projected point (such as having each such line intersect all others at the projected point). Intersections amongst these straight lines and the contour are used to evaluate corrections to the dose at the point. These teachings will accommodate identifying line segments that are located within the contour and that are bound by the intersections with the contour. Elementary contributions as correspond to each of these line segments can be averaged to evaluate delivered dose corrections that are due to the presence of beam-limiting and beam-shaping devices in the particular treatment plan.

14 Claims, 6 Drawing Sheets

METHOD AND APPARATUS TO PROVIDE CORRECTIONS FOR A RADIATION-THERAPY BEAM

TECHNICAL FIELD

This invention relates generally to radiation therapy and more particularly to the use of patient collimators.

BACKGROUND

Radiation therapy is known in the art and serves a variety of medical purposes. Though some therapies involve exposing a patient's entire body to radiation (for example, when preparing a patient to receive a bone marrow transplant), in most cases the intent is to limit the radiation dosing to only specific areas of the patient's body (often referred to as a treatment volume). Various beam-limiting and/or beam-shaping devices are used for this purpose.

Such devices are located between the source and the patient; in some instances, they may be positioned very close to the source of radiation (e.g., primary collimator) while in other cases, they may be placed very close to the patient. The latter are sometimes referred to as patient collimators or blocks (hereinafter, the expression "block" will be used to refer to such a patient-proximal device). These blocks are made of a material (such as lead) that will efficiently block the radiation beam, save for an area or areas corresponding to one or more apertures formed through the material, to permit the beam to pass therethrough.

Ideally, such a block will frame the treatment volume in a manner that exposes only portions of the patient's body that require radiation treatment while preventing such exposure for other portions of the patient's body. The various treatment plans created for a given patient are evaluated on the basis of their success in delivering the prescribed dose to the target (and minimizing the dose in the surrounding healthy tissue); in this context, the correct shape and placement of the various collimators are typically of crucial importance.

The aperture design comprises a first-order effect with respect to the efficacy of a given radiation therapy treatment plan. There are, however, other potentially important contributing factors that have been (so far) overlooked in clinical applications. The fact that the block has a non-zero thickness is one such factor (as typical prior art planning reduces the block to a two-dimensional object (by disregarding its thickness) for computational simplicity). Another such factor is scattering of the beam off the material of the block. Though the fact that such effects induce higher-order influences, they may nevertheless induce sizable corrections to the local dose (e.g., to the dose delivered outside the target or at its margins).

BRIEF DESCRIPTION OF THE DRAWINGS

The above needs are at least partially met through provision of the method and apparatus to provide corrections for a radiation-therapy beam described in the following detailed description, particularly when studied in conjunction with the drawings, wherein.

Figure 1:
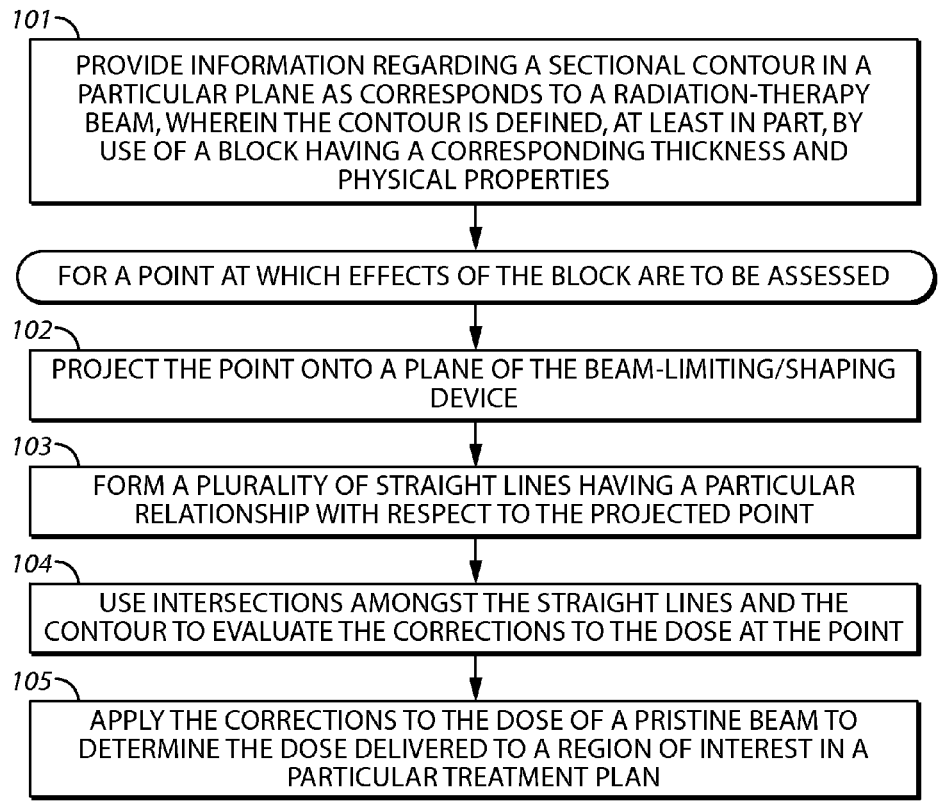
FIG. 1 comprises a flow diagram as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments are suitable for use in providing corrections that apply to the delivered dose in radiation therapy. Information is provided regarding a sectional contour in a particular plane as corresponds to a radiation-therapy beam (wherein the contour is defined, at least in part, by use of a block having a corresponding thickness and physical properties (such as, but not limited to, beam-scattering properties)). Then, for a point at which effects of the block are to be assessed (such as a point within the treatment volume or external to the treatment volume (such as adjacent to the treatment volume, either on a side thereof or closer to the entrance region)), certain actions are taken.

In particular, the point is projected onto the plane of the (downstream face of the) block. A plurality of straight lines is then formed, where each line has a particular relationship with respect to the projected point. By one approach, this can comprise having each such line intersect all others at the projected point. Intersections amongst these straight lines and the aforementioned contour are then used to evaluate the corrections to the dose delivered at the original point. These corrections can then be applied to the dose of the pristine beam, to determine the dose delivered to the region of interest in a particular treatment plan.

By one approach, these teachings will accommodate identifying line segments that are located within the contour and that are bound by the intersections with the contour. Elementary contributions as correspond to each of these line segments are then averaged to thereby evaluate the dose corrections.

Those skilled in the art will appreciate that these teachings permit higher-order effects (such as those attributable to non-zero thickness materials, beam scattering, and so forth) to be taken into account for medically-related radiation therapy treatment plans in a way that avoids computational complexity and that can be begun and completed in a relatively brief period of time. This, in turn, makes these teachings suitable for use in modern therapeutic applications where time is an important factor.

These and other benefits may become clearer upon making a thorough review and study of the following detailed description. Referring now to the drawings, and in particular to FIG. 1, an illustrative process that is compatible with many of these teachings will now be presented.

Figure 2:
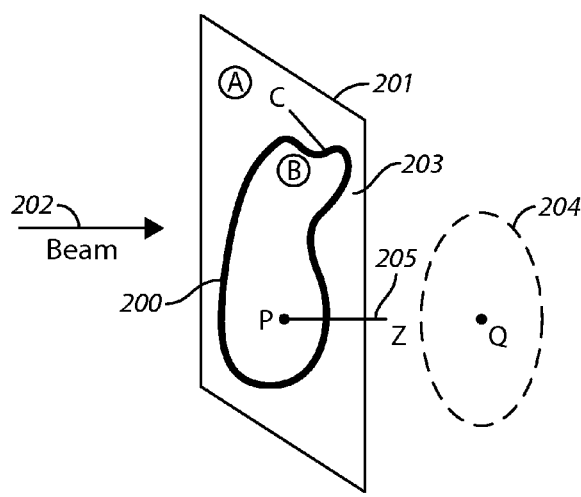
FIG. 2 comprises a perspective schematic view as configured in accordance with various embodiments of the invention.

Referring now to FIGS. 1 and 2, this process 100 includes the step 101 of providing information regarding a sectional contour 200 in a particular plane 201 as corresponds to the lateral extents of the radiation-therapy beam 202. These teachings are applicable for use with a wide variety of beams including but not limited to photon beams, proton beams, electron beams, heavy-ion beams, and so forth. This contour 200 is defined, at least in part, by use of a block 203 having a corresponding thickness (not shown in FIG. 2) and other physical properties such as, but not limited to, the beam-scattering properties of the material that comprises the block 203. More precisely, this contour 200 corresponds to the outlines of the block's aperture and hence represents an area where the beam 202 can pass, in pristine form. The provision of such information comprises a known area of endeavor. As these the present teachings are not overly sensitive to the selection of any particular approach in these regards, for the sake of brevity further elaboration regarding the provision of such information will not be presented here.

This process 100 then provides for a number of actions to be taken with respect to a point at which effects of the block 203 are to be assessed. For purposes of illustration and not by way of limitation, this description will presume that these effects comprise effects that are associated with the non-zero thickness of the block 203 along with effects that are associated with the scattering of the beam 202 off the material that comprises the block 203. With continued reference to FIG. 2 as well, in this illustrative example this point is denoted by the letter "Q" and exists within a treatment volume 204 as corresponds to a given patient. Those skilled in the art will appreciate, however, that this point Q could also be located externally of the treatment volume if desired.

This process 100 includes the corresponding step 102 of projecting this point Q onto the aforementioned plane 201 as corresponds to the block 203. This step 102 therefore results in the provision of a projected point denoted in FIG. 2 by the letter "P." In this illustrative example, this projection is along the Z axis 205 (that is, in the direction along which the beam 202 propagates).

Figure 3:
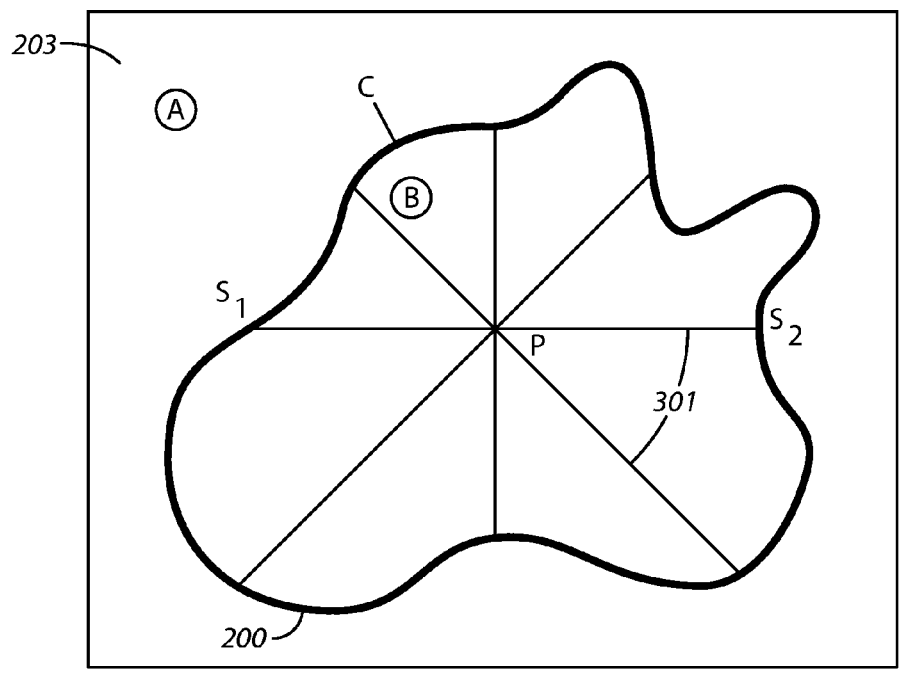
FIG. 3 comprises a front-elevational schematic view as configured in accordance with various embodiments of the invention.

Next, and referring now to both FIGS. 1 and 3, this process 100 presents the step 103 of forming a plurality of straight lines 301. Each of these straight lines 301 has a particular relationship with respect to the projected point P; in this case, each such straight line 301 intersects all other corresponding straight lines at the projected point P. It will be further noted that each such straight line 301 also intersects the contour 200 in at least two locations. These intersections with the contour define corresponding line segments. For example, as shown in FIG. 3, one such line segment is bounded by points $S_1$ and $S_2$.

Figure 4:
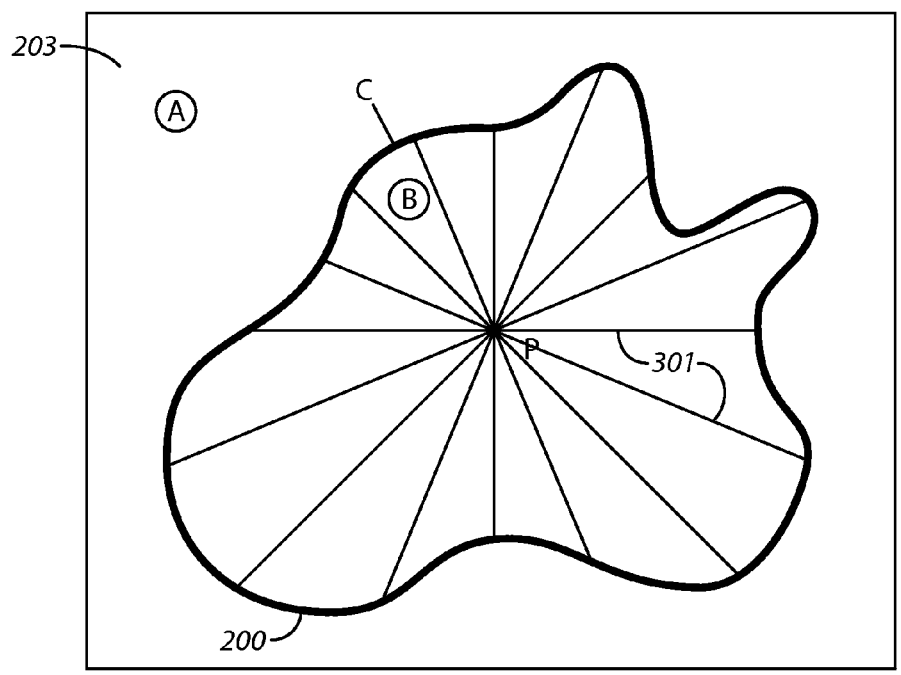
FIG. 4 comprises a front-elevational schematic view as configured in accordance with various embodiments of the invention.

In the illustrative example shown in FIG. 3, four such straight lines 301 are considered. These teachings will accommodate essentially any plurality of such lines. For example, and by way of further illustration, FIG. 4 depicts eight such straight lines 301. Generally speaking, accuracy for the corresponding correction information will improve as the number of straight lines formed in this step 103 increases. That said, however, useful results can be expected in many application settings with a relatively few number of straight lines (such as eight).

It should be noted that there may be an even number of such straight lines or an odd number of such straight lines. It should also be noted that in the examples shown, the straight lines are created in an equiangular manner; while such a configuration contributes to reduced computational complexity, other choices in these regards may be useful to accommodate the needs and/or opportunities as may tend to characterize a given application setting.

Figure 5:
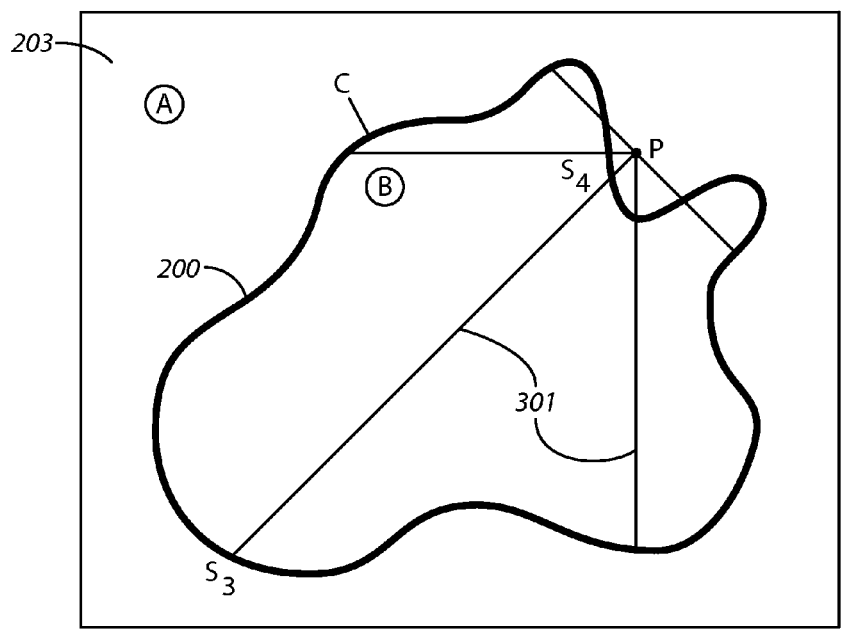
FIG. 5 comprises a front-elevational schematic view as configured in accordance with various embodiments of the invention.
Figure 6:
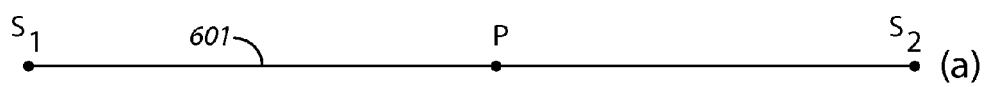
FIG. 6 comprises a schematic view as configured in accordance with various embodiments of the invention.
Figure 6:
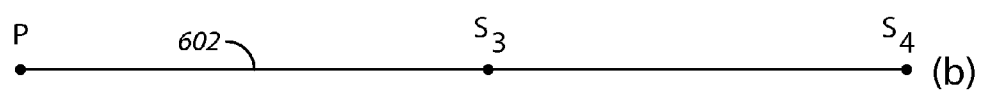

It may further be noted that, in the examples provided above, the projected point P is found within the confines of the contour 200. These teachings will accommodate, however, application settings that dictate otherwise. For example, and as illustrated in FIG. 5, these same steps can be applied when the projected point P exists externally to the contour 200. In this case, however, it can be noted that a given corresponding line segment (such as the line segment denoted by endpoint $S_3$ and $S_4$) will not include the projected point P between its endpoints. To assist in further illustrating this point, FIG. 6 presents a juxtaposition of a first line 601 that includes the projected point P between its endpoints $S_1$ and $S_2$ and a second line 602 where the projected point P is external to its endpoints $S_3$ and $S_4$.

Figure 7:
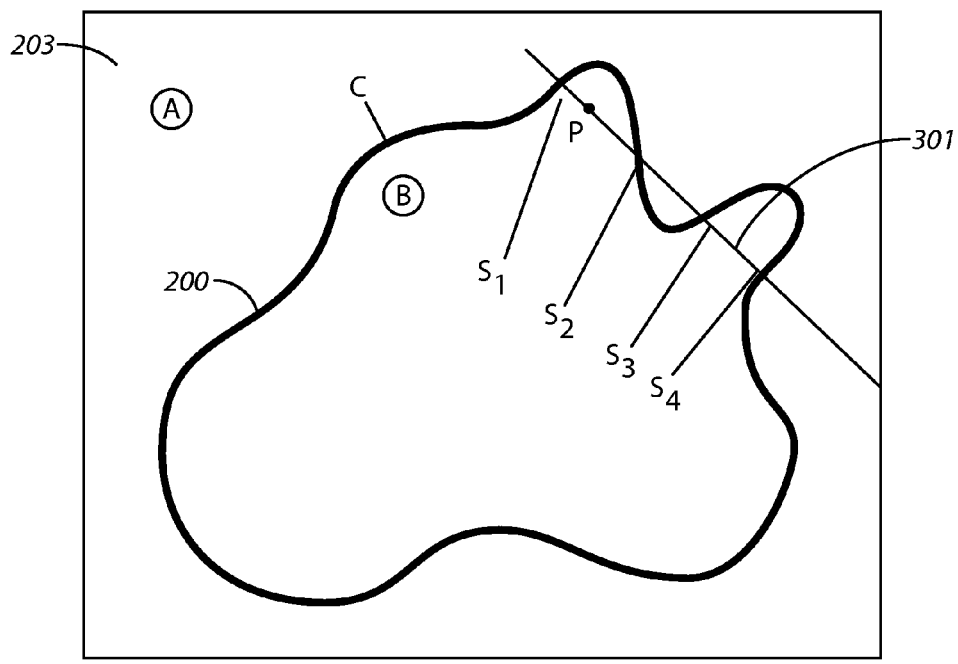
FIG. 7 comprises a front-elevational schematic view as configured in accordance with various embodiments of the invention.

The present teachings will accommodate other possibilities in these regards as well. As just one illustrative example in these regards, and referring now momentarily to FIG. 7, a given straight line 301 may intersect the contour 200 in more than two points when the contour 200 has a shape that dictates such a result. In the example shown, a single straight line 301 has a first line segment defined by endpoints $S_1$ and $S_2$ (and that includes the projected point P as well) and a second line segment defined by endpoints $S_3$ and $S_4$.

With continued reference to FIG. 1, this process 100 also includes the step 104 of using intersections amongst the straight lines 301 and the contour 200 to evaluate the corrections to the dose at the original point Q of interest. In particular, and by way of example, this can comprise taking the aforementioned identified line segments that are located within the contour 200 and that are bound by their intersections with the contour 200 and averaging their elementary contributions. It may be noted here that the elementary contribution of a given line segment (to, of course, the original point Q of interest) will comprise a function of the distance of point Q to the aforementioned plane 201 that contains the line segments.

Those skilled in the art will recognize and understand various ways by which the foregoing can be realized and leveraged. For the sake of illustration in these regards, certain additional details regarding block-thickness corrections will now be offered with respect to these steps. It will be understood that these details are not intended to serve as any expression of limitation with respect to these teachings.

In medical applications, the formal beam-shaper object (sometimes referred to as a DICOM block) that is created at planning time to represent the physical block, comprises the projection of the downstream face (of the block) to a plane (perpendicular to the beam) at isocentre depth. An extension of the physical block is therefore obtained via a simple scaling involving the source-axis (SAD) and block-isocentre (IBD) distances.

Figure 8:
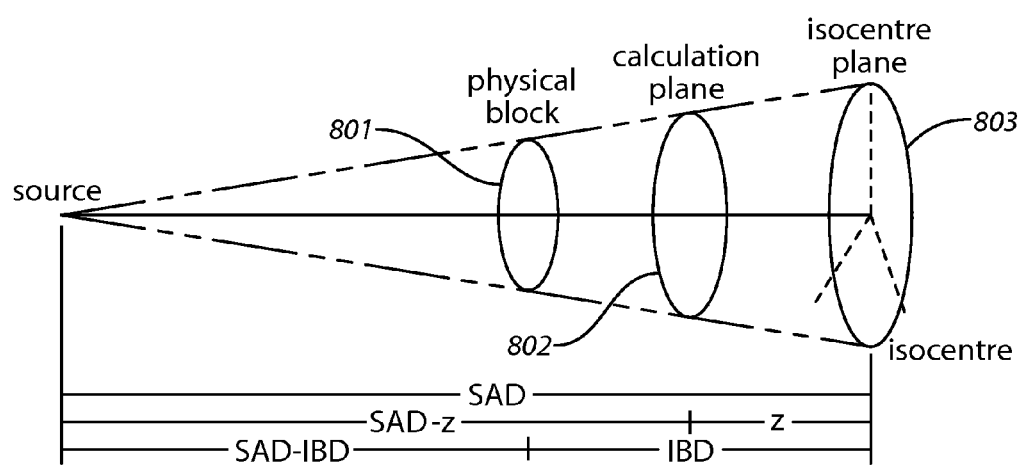
FIG. 8 comprises a side-perspective schematic view as configured in accordance with various embodiments of the invention.

Having retrieved the extension of the block, it is straightforward to obtain the downstream projection at any value for z; in order to obtain the upstream projections, one can use, in addition to the aforementioned quantities, the block thickness (d). The relation between the DICOM block 803 (associated in FIG. 8 with the isocentre plane), the extension 801 (associated in FIG. 8 with the physical block), and the downstream projection 802 (associated in FIG. 8 with the calculation plane) at a specified z position is illustrated in FIG. 8.

The upstream projection is obtained by projecting the extension from depth z=IBD+d. The thin-block approximation (currently used in clinical applications when evaluating the dose) corresponds to d=0 mm (noting that the downstream and upstream projections coincide at all z values).

Assuming that the coordinates of the projected (downstream- or upstream-face, as the case might be) ends of a line segment are denoted as $x_1$ and $x_2$, the contribution of the line segment to the fluence at a point $x_p$ (lying on the straight line defined by $x_1$ and $x_2$) on the calculation plane is given by the formula $$F(x_p) = \frac{1}{2}\left|\mathrm{erf}\left(\frac{x_p - x_1}{\sigma_1 \sqrt{2}}\right) - \mathrm{erf}\left(\frac{x_p - x_2}{\sigma_2 \sqrt{2}}\right)\right|, \quad (1)$$

where erf(x) denotes the error function and $\sigma_{1,2}$ stand for the rms (lateral) spreads of the beam at the specified depth. The quantities $\sigma_{1,2}$ can be obtained via source mirroring according to known prior art methods; as points on the downstream or upstream faces of the block are used, the resulting σ values in Equation 1 are equal only when one block face is involved in the mirroring process.

Figure 9:
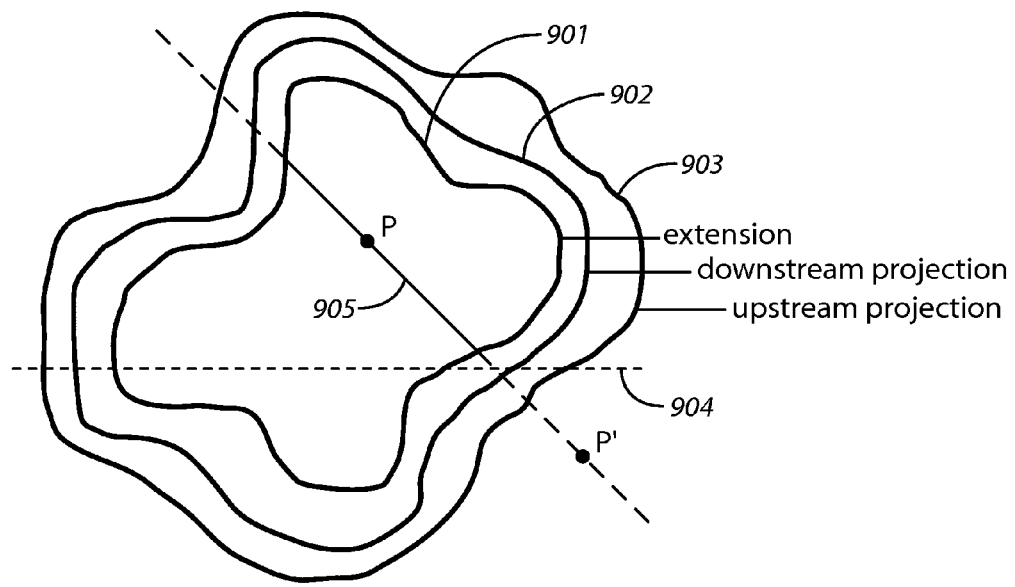
FIG. 9 comprises a front-elevational schematic view as configured in accordance with various embodiments of the invention.

One simple example of the projections on the calculation plane is shown in FIG. 9; the block extension 901 is contained within the downstream projection 902, which (in turn) is contained within the upstream projection 903. (In reality, depending on the complexity of the shape of the block aperture and on the relative position of the central beam axis, these three contours might intersect one another.) The central beam axis intersects the calculation plane at the origin of the x,y coordinate system 904. One line segment 905 is shown along with two points, one within the line segment (P) and the other outside the line segment (P'). The fluence contributions to both points may be evaluated by using Equation 1 with the appropriate $x_{1,2}$ and $\sigma_{1,2}$ values.

Figure 10:
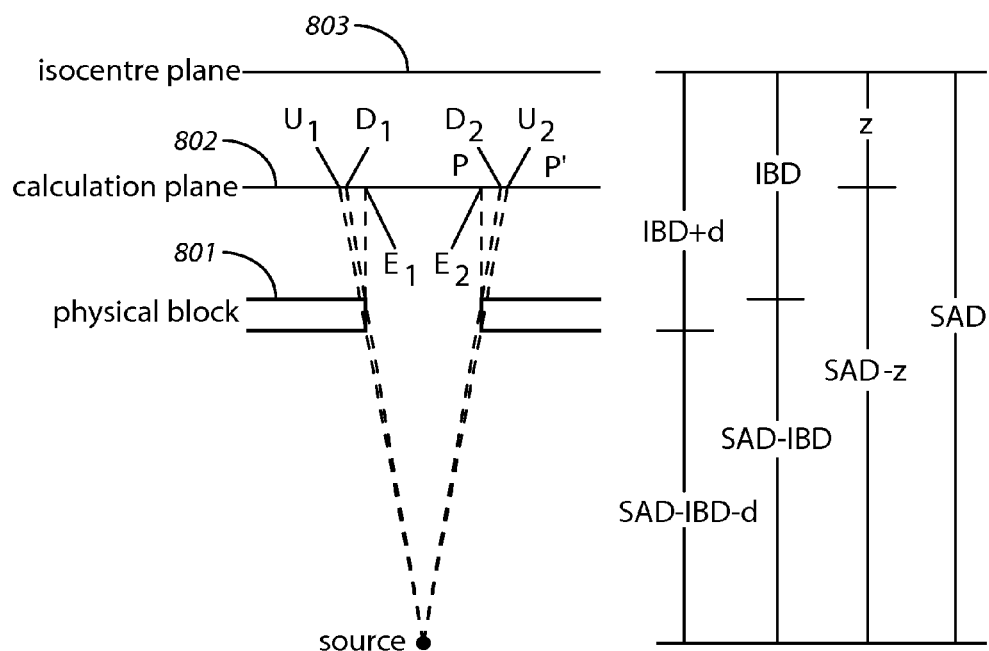
FIG. 10 comprises a side-elevational schematic view as configured in accordance with various embodiments of the invention.

Some important elements for the evaluation of the contribution of a line segment to the fluence at a specified point on the calculation plane are illustrated in FIG. 10. Although, in the general case, the line segment does not contain the intersection of the x and y axes of FIG. 9, all lengths (which are important to these purposes) scale by the same factor, thus enabling the simplified picture shown here.

The coordinates of the projected points $U_1$, $D_1$, $D_2$, and $U_2$ are obtained on the basis of FIG. 10 via simple operations. It is known in the art that protons whose tracks project inside the aperture extension onto the plane of interest see the upstream face as the limiting boundary. Only for protons whose tracks end up outside the aperture on the plane of interest is the downstream face the limiting aperture boundary. In fact, this statement applies to the case of a half-block (that is, a one-sided block).

The modification, however, in the case of a line segment as proposed herein is straightforward. First, points within the extension of the aperture see the upstream face of the line segment as the limiting boundary, and second, points outside the extension of the miniblock see one upstream and one downstream edge as limiting boundaries.

Obviously, in order to evaluate the fluence at the point P as appears in FIG. 10, one has to use the coordinates of the projected points $U_1$ and $U_2$, along with the source size using the upstream face of the bock in the mirroring process. On the other hand, to evaluate the fluence at P', one can use $U_1$ along with the source size when using the upstream face of the block in the mirroring process (contribution of the "left" part of the line segment) and $D_2$ along with the source size when using the downstream face of the block in the mirroring process (contribution of the "right" part of the line segment). This simplified picture, featuring what a point "perceives" as limiting boundaries, suffices in obtaining the appropriate fluence contributions.

Figure 11:
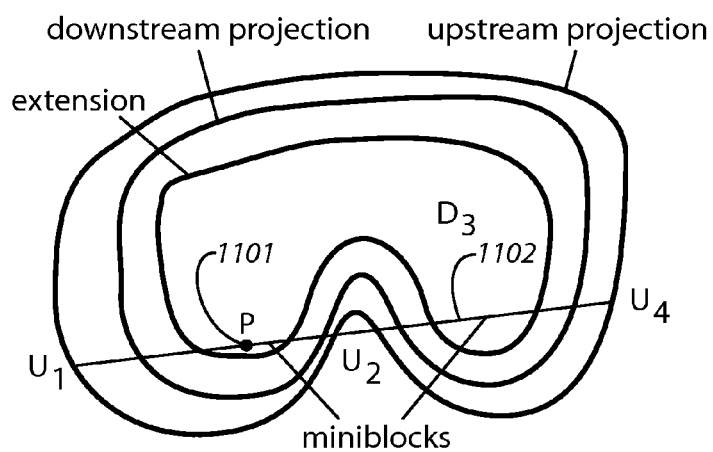
FIG. 11 comprises a front-elevational schematic view as configured in accordance with various embodiments of the invention.

Finally, the number of contributions which a point will receive depends on the geometry and on the shape of the block. One example of a point receiving two contributions in a given direction is shown in FIG. 11; the point P lies within the extension of the line segment 1101 on the left and outside the extension of the line segment 1102 on the right.

Figure 12:
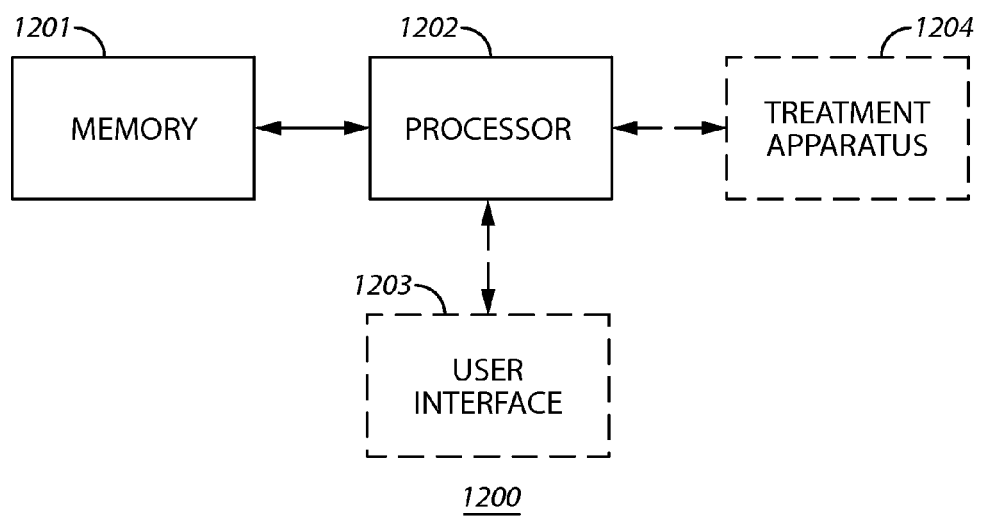
FIG. 12 comprises a block diagram as configured in accordance with various embodiments of the invention.

Those skilled in the art will appreciate that the above-described processes are readily enabled using any of a wide variety of available and/or readily configured platforms, including partially or wholly programmable platforms as are known in the art or dedicated-purpose platforms as may be desired for some applications. Referring now to FIG. 12, an illustrative approach to such a platform will now be provided.

In this illustrative example, an apparatus 1200 to facilitate providing corrections with respect to applying a dose of radiation comprises a memory 1201. This memory 1201 has stored therein the aforementioned information regarding the sectional contour in a particular plane as corresponds to a radiation-therapy beam as described above. It will be recalled that this contour is defined, at least in part, by use of a block (such as a patient collimator) having a corresponding thickness and certain physical properties as well.

This memory 1201 operably couples to a processor 1202. Those skilled in the art will recognize and appreciate that such a processor 1202 can comprise a fixed-purpose hard-wired platform or can comprise a partially or wholly programmable platform. All of these architectural options are well known and understood in the art and require no further description here. It will also be understood that this processor 1202 can comprise a stand-alone platform or can also serve additional functionality as desired.

This processor 1202 can be configured (using, for example, programming as will be well understood by those skilled in the art) to carry out one or more of the steps, actions, and/or functions as are described herein. This can include, for example, projecting the aforementioned point onto a plane of the block, forming a plurality of straight lines having a particular relationship with respect to the projected point (such as, for example, intersecting therewith), and then using intersections amongst the straight lines and the contour to evaluate the corrections to the dose at the point.

To facilitate such capabilities, if desired, this processor 1202 can further couple to a user interface 1203 and/or the treatment apparatus 1204 that is to receive the correction information. This user interface 1203 can serve, for example, to provide an input mechanism by which an end user can provide information to the processor 1203 and/or an output mechanism by which the processor 1202 can provide information to an end user.

Those skilled in the art will recognize and understand that such an apparatus 1200 may be comprised of a plurality of physically distinct elements as is suggested by the illustration shown in FIG. 12. It is also possible, however, to view this illustration as comprising a logical view, in which case one or more of these elements can be enabled and realized via a shared platform. It will also be understood that such a shared platform may comprise a wholly or at least partially programmable platform as are known in the art.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. As one example in this regard, it will be understood and appreciated that these teachings can be applied to any type of beam-limiting and/or beam-shaping device and not just the aforementioned patient collimator.

I claim:

1. A method to provide corrections to apply to a dose, comprising:
    providing information regarding a sectional contour in a particular plane as corresponds to a radiation-therapy beam, wherein the contour is defined, at least in part, by use of a patient collimator having a corresponding thickness and physical properties;
    for a point at which effects of the patient collimator are to be assessed:
        projecting the point onto a plane;
        forming a plurality of straight lines having a particular relationship with respect to the projected point by, at least in part, forming a plurality of straight lines that intersect one another at the projected point and wherein at least some of the straight lines intersect the contour in at least two locations along the periphery;
        using intersections amongst the straight lines and the contour to evaluate the corrections to the dose at the point by, at least in part, identifying line segments that are located within the contour and that are bound by the intersections with the contour to yield well-defined line segments;
    applying the corrections to the dose of a pristine beam to determine the dose delivered to a region of interest in a particular treatment plan.

2. The method of claim 1 wherein the radiation-therapy beam comprises a photon beam.

3. The method of claim 1 wherein the radiation-therapy beam comprises at least one of the group comprising:
    a proton beam;
    an electron beam;
    a heavy-ion beam.

4. The method of claim 1 wherein the point comprises a point within a treatment volume.

5. The method of claim 1 wherein the point comprises a point external to a treatment volume.

6. The method of claim 1 wherein the physical properties comprise, at least in part, beam-scattering properties.

7. The method of claim 1 wherein using intersections amongst the straight lines and the contour to evaluate the corrections to the dose at the point further comprises averaging elementary contributions as correspond to each of the line segments.

8. An apparatus to, at least in part, facilitate providing corrections with respect to applying to a dose, comprising:
    a memory having stored therein information regarding a sectional contour in a particular plane as corresponds to a radiation-therapy beam, wherein the contour is defined, at least in part, by use of a patient collimator having a corresponding thickness and physical properties;
    a processor that is operably coupled to the memory and that is configured to, for a point at which effects of the patient collimator are to be assessed:
        project the point onto a plane;
        form a plurality of straight lines having a particular relationship with respect to the projected point by, at least in part, forming a plurality of straight lines intersecting at the projected point wherein at least some of the straight lines intersect the contour in at least two locations along the periphery;
        use intersections amongst the straight lines and the contour to evaluate the corrections to the dose at the point by, at least in part, identifying line segments that are located within the contour and that are bound by an intersection with the contour to provided identified line segments.

9. The apparatus of claim 8 wherein the radiation-therapy beam comprises a photon beam.

10. The apparatus of claim 8 wherein the radiation-therapy beam comprises at least one of the group comprising:
    a proton beam;
    an electron beam;
    a heavy-ion beam.

11. The apparatus of claim 8 wherein the point comprises a point within a treatment volume.

12. The apparatus of claim 8 wherein the point comprises a point external to a treatment volume.

13. The apparatus of claim 8 wherein the physical properties comprise, at least in part, beam-scattering properties.

14. The apparatus of claim 8 wherein the processor is configured to use intersections amongst the straight lines and the contour to evaluate the corrections to the dose at the point further by averaging elementary contributions as correspond to each of the line segments.

* * * * *